(12) United States Patent
Poirrier et al.

(10) Patent No.: US 9,044,567 B2
(45) Date of Patent: Jun. 2, 2015

(54) PHOTOTHERAPY METHOD AND DEVICE

(75) Inventors: Robert Poirrier, Beaufays (BE); Vincent Moreau, Theux (BE)

(73) Assignee: Constructions Electriques Schreder, Fernelmont (BE)

( * ) Notice: Subject to any disclaimer, the term of this patent is extended or adjusted under 35 U.S.C. 154(b) by 1791 days.

(21) Appl. No.: 10/599,520

(22) PCT Filed: Mar. 30, 2005

(86) PCT No.: PCT/EP2005/051430
§ 371 (c)(1),
(2), (4) Date: May 11, 2007

(87) PCT Pub. No.: WO2005/094941
PCT Pub. Date: Oct. 13, 2005

(65) Prior Publication Data
US 2007/0233207 A1    Oct. 4, 2007

(30) Foreign Application Priority Data
Mar. 31, 2004    (BE) .................................. 2004/0167

(51) Int. Cl.
*A61N 5/06* (2006.01)
*A61M 21/00* (2006.01)

(52) U.S. Cl.
CPC ....... *A61M 21/00* (2013.01); *A61M 2021/0044* (2013.01); *A61N 5/0618* (2013.01); *A61N 2005/0648* (2013.01)

(58) Field of Classification Search
USPC ............................................. 607/88; 128/898
See application file for complete search history.

(56) References Cited

U.S. PATENT DOCUMENTS

| | | | | |
|---|---|---|---|---|
| 4,782,819 A * | 11/1988 | Adair | ............................. | 600/109 |
| 5,292,345 A * | 3/1994 | Gerardo | ........................... | 607/88 |
| 5,709,645 A * | 1/1998 | Siever | .............................. | 600/27 |
| 5,923,398 A * | 7/1999 | Goldman | ...................... | 351/203 |
| 6,040,946 A * | 3/2000 | Hebert | ........................... | 359/630 |
| 6,053,936 A * | 4/2000 | Koyama et al. | ................ | 607/88 |
| 6,092,906 A * | 7/2000 | Olmstead | ...................... | 362/105 |
| 6,235,046 B1 * | 5/2001 | Gerdt | .............................. | 607/88 |
| 6,299,632 B1 * | 10/2001 | Jaillet | ............................. | 607/88 |
| 6,715,150 B1 * | 4/2004 | Potin | .................................. | 2/15 |
| 7,422,327 B2 * | 9/2008 | Smith | ........................... | 351/206 |
| 2002/0026188 A1 * | 2/2002 | Balbierz et al. | ................. | 606/41 |
| 2004/0225340 A1 * | 11/2004 | Evans | ............................ | 607/88 |
| 2006/0258100 A1 * | 11/2006 | Mukunoki | .................... | 438/262 |
| 2007/0171368 A1 * | 7/2007 | Smith | ........................... | 351/206 |

FOREIGN PATENT DOCUMENTS

| | | |
|---|---|---|
| EP | 0 302 035 | 2/1989 |
| WO | WO 89/08476 | 9/1989 |
| WO | WO 90/10473 | 9/1990 |
| WO | WO 91/14475 | 10/1991 |

(Continued)

*Primary Examiner* — William Thomson
*Assistant Examiner* — Jeffrey Lipitz
(74) *Attorney, Agent, or Firm* — McCracken & Gillen LLC

(57) ABSTRACT

A phototherapy method, acting on the eyes (5) of an individual through light rays (R) of at least one specific wavelength, emitted by at least one light source (3) stationary relative to his/her head, which consists in: arranging the light source (3) at the periphery of his/her visual field allowing the individual's normal activities and in deflecting the light rays (R) onto a specific zone (9) of the retina (11), so as to maintain vision.

13 Claims, 2 Drawing Sheets

(56) References Cited

FOREIGN PATENT DOCUMENTS

| WO | WO 94/09851 | 5/1994 |
| WO | WO 02/074176 | 9/2002 |
| WO | WO 2004/096364 | 11/2004 |

* cited by examiner

PHOTOTHERAPY METHOD AND DEVICE

PRIORITY CLAIM

This patent application is a U.S. National Phase of International Application No. PCT/EP2005/051430, filed Mar. 30, 2005, which claims priority to Belgian Patent Application No. 2004/0167, filed Mar. 31, 2004, the disclosures of which are incorporated herein by reference in their entirety.

FIELD OF THE INVENTION

The present invention relates to a phototherapy method, acting on the eyes of an individual through light rays of at least one specific wavelength, the rays being emitted by at least one light source which is stationary relative to his head.

BACKGROUND OF THE INVENTION

Phototherapy applied to humans seems to be an effective treatment, in particular with regard to Seasonal Affective Disorder which is a form of depression, the main characteristic of which is that it occurs during the same period each year, usually at the start of autumn or winter and lasting through to spring.

Applied to an individual, phototherapy (sometimes known as luminotherapy) may consist in exposure to bright light (between 2500 and 10000 lux on the cornea) for a certain period of time and in a controlled environment. The information relating to this light, which is detected by the eyes, is then transmitted via the optical nerve to the suprachiasmatic nucleus of the hypothalamus which controls the neurological and endocrine circadian rhythms, with an effect on the concentration, mood, and physical and psychological performance of the individual.

Melatonin is one of the favoured markers of the effects of light on the suprachiasmatic nucleus and the epiphysis.

Important photometric parameters for effective treatment are therefore
- the luminous flux proportional to the amount of photons received by the human eye per unit time, expressed either in lumens or in watts,
- the incident light, defined as the luminous flux per unit surface area and expressed either in lux or in watt/m2,
- the amount of light, defined by multiplying the light by the duration of exposure and expressed in lux.s.

Phototherapy devices are primarily known in two forms, namely:
- non-portable lighting units which require the individual being treated to remain in one place during each exposure session and which, if the individual wishes for example to read during this time, exhibit a considerable loss of effectiveness due to the fact that the individual lowers his eyelids which then form a screen against the treatment light, and
- portable lighting units which are fixed to the head in the manner of a helmet or headband or in the form of spectacles, which either supply light to the eyes directly from above and suffer from the same problem concerning the eyelids as forms an obstacle to the aforementioned light when the individual wishes in particular to read, or do not allow any activity since they inundate the entire field of vision with light.

SUMMARY OF THE INVENTION

The aim of the present invention is to overcome the drawbacks of the known devices, and to this effect has the following objectives:

- the light source and its power supply must be light and of small size. They are associated with a control unit which makes it possible to adjust the flux emitted by the source and the operating time. This unit is separate from the therapeutic lighting means and is portable (for example can be worn on a belt),
- the means for supplying light to the eyes must be light and discreet. In order to reduce any losses in terms of light power, this system is located as close to the user's eye as possible. An elegant solution consists in giving it the form of a pair of non-corrective spectacles, which can be fitted onto a pair of corrective spectacles and can supply a therapeutically effective amount of light,
- the lighting means is sufficiently transparent so as to allow the patient to carry out various semi-sedentary activities during the treatment (reading, working or Internet surfing, safe movements, etc.),
- the light spectrum delivered by the lighting means must contain one or more selected wavelengths, or all the wavelengths, of visible light while ensuring that harmful ultraviolet and infrared rays are screened out. This spectrum must be adapted as a function of results of studies with a view to optimising treatment by means of phototherapy,
- finally, the cost of manufacturing the device as a whole must be low enough to allow it to be offered at a favourable price compared to that of the known (stationary or portable) devices.

To this end, the present invention proposes a method which consists in arranging the light source at the periphery of the field of vision so as to allow the usual activities of the individual, and in deflecting said light rays onto a specific zone of the retina so as to maintain vision.

This arrangement is of course advantageously applied to both eyes of the individual to be treated, if these are both able to receive this light in a useful manner.

In one embodiment of the invention, said zone which receives the deflected rays is selected in such a way as to exclude the fovea regardless of the direction of vision below a plane passing through the optical axes of lenses arranged so as to deflect the light rays towards said specific zone. Activity therefore remains possible, the fovea being the most sensitive zone of the eye which allows fine vision and analysis of details during the aforementioned semi-sedentary activities.

Advantageously, the deflected light rays are made to converge in the eye at a point located slightly behind the pupil of the eye. This convergence of the rays entering the eyeball makes it possible to illuminate an extensive surface on the retina, even when the eye changes its direction of vision within the aforementioned limits, and therefore substantially increases the beneficial effect of these rays.

Preferably, the light rays are deflected by diffraction.

The present invention also relates to a device for implementing the phototherapy method of the invention.

According to the invention, the device comprises a support designed to be immobilised on the head, and also the light source(s) mounted on the support at the periphery of the field of vision, emitting light rays of at least one specific wavelength and being arranged so that these rays are directed into the eyes, by deflection means, onto said specific zone. Although white light, without UV or infrared, may be suitable, a selection from blue seems to have a certain benefit. Among other things, an iridescence given by white light, by diffraction, disappears when a colour is selected.

In one embodiment of the invention, said support consists of a spectacle frame, said deflection means being in the form of spectacle lenses.

In one preferred embodiment of the invention, said device comprises, for each eye, one or more light sources, such as light-emitting diodes, and separate deflection means which are arranged so as to cooperate with the light source(s) of each eye.

Advantageously, there is for each light source a condenser which is arranged so as to direct the light rays emitted by each of the sources onto said deflection means, and which is associated with the light source at the periphery of the field of vision.

Preferably, the deflection means consist of a diffractive lens, such as an off-axis diffractive optical element, for each eye.

Other details and special features of the invention will become apparent from the dependent claims and from the description of the drawings which are appended to the present text and which illustrate, by way of non-limiting examples, the method and some particular embodiments of the device according to the invention.

BRIEF DESCRIPTION OF THE DRAWINGS

In the different figures, the same references denote identical or similar elements.

DESCRIPTION OF THE INVENTION

In order to facilitate the explanation and comprehension of the invention, the device of the invention will be described, before the method, within the context of its application to an individual, without this limiting either the possibility of application to animals or the method of the invention.

A device for implementing the phototherapy method according to the invention comprises (FIG. 1) a support 1 designed to be immobilised on the head (not shown) of an individual.

Figure 2:
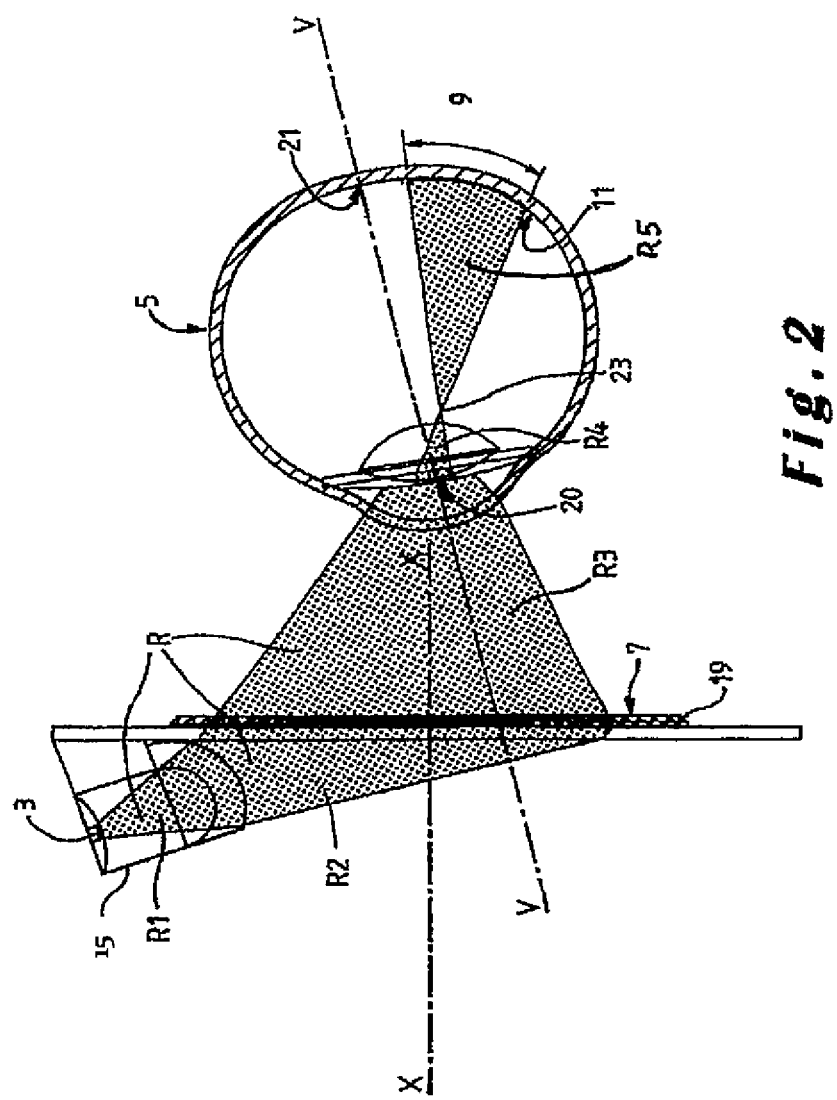
FIG. 2 schematically shows, in vertical section, a path of light rays from a light source of the device of the invention to the back of the eye of an individual equipped with this device.

One or more light sources 3 are mounted on the support 1 at the periphery of the field of vision of the individual. The sources 3 emit light rays R (FIG. 2) of at least one specific wavelength, and they are arranged so that these rays R are directed into the eyes 5 of the individual, by deflection means 7, onto a specific zone 9 of the retina 11.

The aforementioned support 1 may consist of a spectacle frame 12, said deflection means 7 then being in the form of lenses 13 of these spectacles. In this case, these may be corrective lenses, but it is preferable if these lenses are not corrective, in particular for use by individuals who do not wear corrective lenses, so as to facilitate manufacture and reduce stocks of lenses.

It should be noted that, in the present description, the term "lens" should be understood to mean any transparent object, which may or may not be corrective, which is able to be mounted in a spectacle frame or other support 1, in front of the eyes 5, and through which it is possible to see, regardless of its material, its colour, etc.

According to one variant of the invention, the support 1 may consist on the one hand of a conventional spectacle frame 12 with corrective lenses and on the other hand of a spectacle attachment (not shown) which is known per se, in particular in the form of an element which can be equipped with non-corrective sunglass lenses and which is able to be fixed in a removable manner to corrective spectacles. Said deflection means 7 are then in the form of lenses 13 of said attachment, and the light source(s) 3 are mounted on this attachment.

In one embodiment (not shown) of the invention, the spectacles may also be formed in the manner of skiing goggles and may comprise just one lens or screen produced as one piece in front of both eyes, as is known per se. The light source(s) 3 may then be grouped together for example above the nose of the individual wearing these goggles.

Preferably, the device according to the invention may comprise, for each eye 5:
  one or more light sources 3, in particular four per eye as shown in the figures, these preferably being light-emitting diodes due to reasons of size, weight and power consumption, and
  separate deflection means 7 which are arranged so as to cooperate with the light source(s) 3 of each eye 5.

Light-emitting diodes are selected since they can have the following features for the application developed:
  their energy efficiency (power emitted/power consumed) is one of the most advantageous among the various types of light source available,
  it is currently possible to find on the market diodes of all colours, from ultraviolet to infrared,
  the light fluxes emitted can be up to at least ten or so lumens for the most powerful,
  the heat given off by these sources 3 is very low; they can therefore be placed on the spectacle support without any problem,
  the service life of light-emitting diodes exceeds 100,000 hours,
  they are relatively inexpensive.

Size constraints lead to the use of diodes of the SMD (Surface Mounted Device) type.

In order to increase the efficiency or light output of the device of the invention, said device advantageously comprises, preferably separately for each light source 3, a condenser 15 which is arranged so as to direct the light rays R emitted by each of the sources 3 onto said deflection means 7, and which is associated with said light source 3 at the periphery of the field of vision of the individual equipped with the device of the invention. Fresnel lenses may be used to construct a condenser 15 of minimal size and to obtain a luminous flux which is distributed optimally on the deflection means 7.

Figure 1:
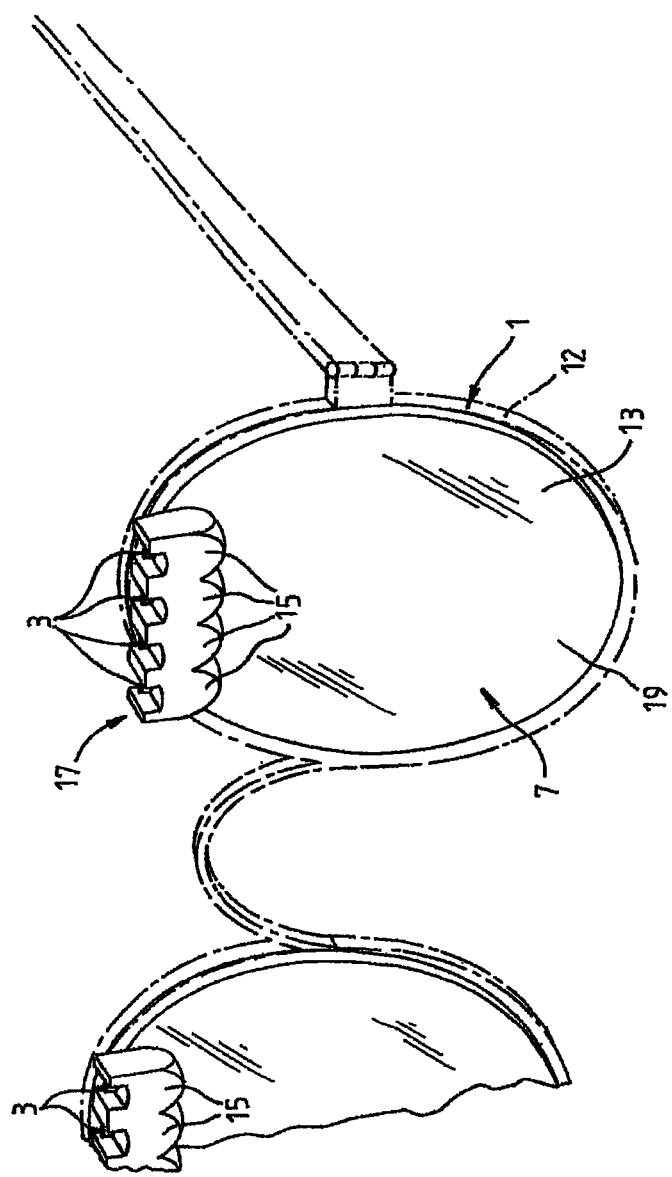
FIG. 1 schematically shows a device of the invention in a broken-away perspective view.

FIG. 1 shows an embodiment comprising, for each eye 5, a one-piece assembly 17 which in each case groups together the four condensers 15 arranged between the four light-emitting diodes and the corresponding deflection means 7. On the diode side, this one-piece assembly 17 is dish-shaped opposite each diode so as to at least partially surround the light-emitting face thereof and to channel a maximum number of rays towards said deflection means 7.

The deflection means 7, fixed at the location of the spectacle lenses 13, may consist, for each eye 5, of a known ridged refractive lens of the Fresnel type with close ridges, as will be understood by those skilled in the art.

However, it is preferred if the deflection means 7 consist of a diffractive lens 19, such as an "off-axis diffractive optical element", for each eye 5. There is presently known, under the term DOE (Diffractive Optical Element), diffractive elements in which, by passing through a microstructure medium, an incident light wave front is split into a multitude of small secondary waves which, by recombining, will form a completely new wave front. The choice of material for these diffractive elements is vast: glass, various synthetic materials, etc.

The production of an off-axis diffractive lens 19 with a high F number may involve a process of holographic recording in a photosensitive resin (of the type used in microelectronics). The principle consists in causing interference between two coherent wave fronts, one planar and the other spherical. This interference results in a modulation, on the micrometer scale, of the light which falls on a thin layer of photosensitive resin deposited on a glass substrate. Chemical development makes it possible to dissolve the parts that have received a high amount of light, producing the desired modulation of the thickness of the developed resin layer.

Mass production of surface-relief diffractive gratings is a problem which has today been overcome by a number of manufacturers. The development of optical supports for storing information, and in particular the compact disc and the DVD, have largely contributed to this know-how. Current replication techniques reach a resolution on the nanometer scale, and the cost of a replica is relatively independent of the complexity of the original microstructure.

If desired, replicas of the original component can be produced independently of said glass substrate and have an adhesive face so as to be able to be subsequently stuck to a spectacle lens 13, for example a corrective spectacle lens, before installing the light sources 3, condensers 15, etc. on the same spectacles.

The aforementioned diffractive lenses 19 can be characterised according to various criteria. The geometric characteristics (engraving depth, grating pitch, shape factor) are of critical importance when selecting large-scale reproduction methods. It should be noted that, in the case of an aforementioned diffractive lens, contrary to that of a linear network, these parameters are not constant over the entire surface of the lens. The optical properties, mainly the diffraction efficiency, make it possible to evaluate the luminous losses of the system.

The following table shows, by way of example, values for the aforementioned criteria:

| | |
|---|---|
| Maximum period | 1 μm |
| Minimum period | 0.4 μm |
| Engraving depth | 0.4 μm |
| Shape factor (depth/period) | from 0.4 to 1 |
| Focal length | 35 mm @ 514.5 nm |
| Diffraction efficiency (diffracted flux/incident flux) | between 30% and 37% |

By looking at the value measured for the diffraction efficiency, it can be seen that a third of the luminous flux that hits the diffractive lens 19 is effectively redirected towards the pupil 20 of the person wearing said lens. This value may seem low but it must be compared with a theoretical calculated maximum value of 41%. Moreover, too high a value for the diffraction efficiency would hypothecate the relative transparency of the present spectacle lens 19 and would make it less convenient to use.

The condenser 15 for the light rays is advantageously arranged so as to direct said rays R onto the face of the corresponding diffraction lens 19 at an angle of incidence of around 70° with respect to the optical axis X-X of this lens, the distance separating the latter from the eye 5 being such that the actual image 23 of the light source is located in the eye 5, slightly behind the pupil 20 thereof.

An F number of the diffractive lens 19 of around 0.7 proves to be a favourable choice.

Relatively precise adjustment of different distances may significantly increase the efficiency of the device of the invention, so as to receive the rays R at the correct locations within the eyes 5 in the best way possible. To this end, the spectacle frame may either be adjusted in the usual manner by an optician or may comprise adjustment means which are known per se, in particular in test frames which are used by ophthalmologists and opticians and which make it possible to adjust the distance between lenses, between lenses and eyes, etc.

As a variant to the figures and to the explanations given above, the diffracting surface area of the diffractive lenses 19 may be reduced, in particular by reducing the hologram formed thereon, so as to occupy only the upper part of the lens 13 in the figures, in order to provide the wearer with even better vision through the lower, untreated portion of the lens for the purpose of reading, etc.

In another variant, the surface area of the lens 19 itself may be reduced by eliminating its lower part so as at that point too to allow the vision of the person wearing the device of the invention.

The appended drawings show a case which seems favourable at present, in which the sources 3 are above the eyes 5, the rays R are deflected so as to converge in the eye 5 and spread widely over a specific selected zone 9 below the fovea 21, so that the latter is not affected by these rays R but rather remains available so as to be able to see other things. However, the present invention is not limited to this case and comprises any position and orientation that may be given to the rays R, while adhering to the fact of arranging the sources 3 outside the field of vision and deflecting them onto a zone which is as large as possible and allows the vision of the person wearing the device of the invention.

A unit which is required in order to supply power to and control and/or adjust the light source(s) 3 is not described here due to the fact that it has nothing to do with the unity of invention in terms of its technical features.

It must be understood that the light source(s) 3 and/or the condenser 15 may be fixed directly to the support 1, or indirectly, particularly when the condenser 15 is for example adhesively bonded or fixed in some other way to the lens 13 or to the lens 19, and that optionally the light source(s) 3 are fixed to the condenser 15.

The phototherapy method of the invention therefore acts on the eyes 5 through light rays R of at least one specific wavelength, emitted by at least one source 3 which is stationary relative to the head of the individual to be treated. This method consists in arranging the light source 3 at the extreme periphery of the field of vision so as to allow the usual activities of this individual, and in deflecting said light rays R onto a specific zone 9 of the retina 11, selected so that the individual maintains vision.

It must be understood that the invention is in no way limited to the embodiments described, and that many modifications may be made thereto without departing from the scope of the claims.

Thus, said specific zone 9 which receives the deflected rays is selected in such a way as to exclude the fovea 21 regardless of the direction of vision within a range below the plane passing through the optical axis X-X of the lenses 19. Thus the fovea 21, which is the region of the retina 11 that allows fine vision, is not supplied with light by the deflected rays R and therefore remains available for a whole range of activities that do not require the use of peripheral vision (such as reading, working on a screen, movements within a safe environment, etc.).

In order to optimise said method, the deflected light rays R are made to converge in the eye 5 at a point 23 (actual image of the source) located slightly behind the pupil 20 of the eye 5.

As a result of this choice, regardless of the angle of inclination of the eye 5 within the specific range given above, the flux is concentrated on the same region of the retina 11 (lower half in the example shown). This results from the convergence of the rays and the relative position of the cornea and of the focus of the lens 19. Specifically, this means that the "apparent" light source moves along with the direction of vision. If the individual lowers his eyes, it is the lower part of the diffractive grating of the lens 19 which performs the deflection. When the individual is looking at the horizon, it is the upper part of the lens 19 that is involved.

The light rays R (FIG. 2) emitted by the source 3 are spread at R1 in a manner guided in the condenser 15 so as to form a beam at R2, said beam being directed towards the diffractive lens 19. The latter reorients the light rays R to form a beam R3 which converges on the pupil 20 over a zone that is larger than the surface area of the latter. The pupil 20 selects a portion of this zone and allows the passage of a beam R4 that has been deflected by the lenses of the eye (cornea and crystalline lens) so as to form, beyond the actual image 23 of the source 3, the beam R5 which reaches said specific zone 9 of the retina 11.

The method of the invention has just been described in the case where the light rays are deflected by diffraction. However, it is also possible to deflect the light rays by refraction without departing from the scope of the appended claims.

KEY TO THE FIGURES

R light rays (comprising R1 to R5)
X-X optical axis of the lens
V-V axis of vision
1 support
3 light source(s)
5 eye(s)
7 deflection means
9 specific zone of 11
11 retina of 5
12 spectacle frame
13 spectacle lens(es) or similar element(s)
15 condenser
17 one-piece assembly of condensers 15
19 diffractive lens
20 pupil of 5
21 fovea of 5
23 actual image of the light source

The invention claimed is:

1. Phototherapy method, acting on a set of eyes of an individual with a head, each eye comprising a pupil, a retina and a fovea, through light rays of at least one specific wavelength, emitted by at least one light source which is stationary relative to the head of the individual, wherein the method comprises the steps of:
    arranging the light source at the periphery of the field of vision so as to allow the usual activities of the individual; and
    using an off-axis diffractive optical element to deflect said light rays by diffraction onto a specific zone of the retina so as to maintain vision.

2. Method according to claim 1, wherein said limited zone which receives the deflected rays is selected in such a way as to exclude the fovea regardless of the direction of vision below a plane passing through the optical axis of lenses arranged so as to deflect the light rays towards this limited zone.

3. Method according to claim 2, characterised in that the deflected light rays are made to converge in the eye at a point located slightly behind the pupil of the eye, but before the retina.

4. Method according to claim 1, characterised in that the deflected light rays are made to converge in the eye at a point located slightly behind the pupil of the eye, but before the retina.

5. Method according to claim 1, wherein said specific zone of the retina is below the fovea.

6. Device for implementing a phototherapy method on a set of eyes of an individual with a head, each eye comprising a pupil, a retina and a fovea, and comprising:
    a support designed to be immobilised on the head of the individual;
    at least one light source mounted on the support at the periphery of a field of vision of the individual, emitting light rays of at least one specific wavelength and being arranged so that the latter are directed into the eyes, by deflection means, onto a specific zone of the retina; and
    wherein said deflection means comprises at least one off-axis diffractive optical element for each eye.

7. Device according to claim 6, wherein said support consists of a spectacle frame, said deflection means being in the form of spectacle lenses.

8. Device according to claim 6, wherein the support comprises a spectacle frame with corrective lenses and a spectacle attachment, said deflection means being in the form of lenses of said attachment, the at least one light source being mounted on this attachment.

9. Device according to claim 6, wherein the device further comprises, for each eye, one or more light sources, and separate deflection means which are arranged so as to cooperate with the light sources of each eye.

10. Device according to claim 9, wherein the device further comprises, separately for each light source, a condenser:
    which is arranged so as to direct the light rays emitted by each of the sources onto said deflection means; and
    which is associated with the light source at the periphery of the field of vision.

11. Device according to claim 10, wherein the condenser for the light rays is arranged so as to direct said rays onto the face of the corresponding off-axis diffractive optical element at an angle of incidence, with respect to the optical axis of this off axis diffractive optical element, provided such that the distance separating the latter from the eye is such that the actual image of the light source is located in the eye, slightly behind the pupil thereof, but before the retina.

12. Device according to claim 6, characterised in that an F number of the diffractive optical element of around 0.7 is selected.

13. Device according to claim 6, wherein said specific zone of the retina is below the fovea.

* * * * *